(12) United States Patent
Lambiase

(10) Patent No.: US 7,429,483 B2
(45) Date of Patent: *Sep. 30, 2008

(54) USE OF NERVE GROWTH FACTOR FOR THE STORAGE, CULTURE OR TREATMENT OF CORNEA

(75) Inventor: Alessandro Lambiase, Rome (IT)

(73) Assignee: Anabasis S.R.L., Rome (IT)

( * ) Notice: Subject to any disclaimer, the term of this patent is extended or adjusted under 35 U.S.C. 154(b) by 80 days.

This patent is subject to a terminal disclaimer.

(21) Appl. No.: 10/337,853

(22) Filed: Jan. 8, 2003

(65) Prior Publication Data

US 2003/0096413 A1 May 22, 2003

Related U.S. Application Data

(63) Continuation of application No. 09/403,568, filed on Oct. 25, 1999, now Pat. No. 6,537,808.

(51) Int. Cl.
*A01N 1/00* (2006.01)
*C12N 5/00* (2006.01)
*C12N 15/74* (2006.01)
*A61K 31/785* (2006.01)

(52) U.S. Cl. .................. 435/325; 435/1.1; 435/336; 435/384; 424/78.04; 514/2; 514/912; 514/914

(58) Field of Classification Search ............ 514/2, 514/912, 914; 435/325, 1.1, 336, 384
See application file for complete search history.

(56) References Cited

U.S. PATENT DOCUMENTS

| 4,959,319 | A | | 9/1990 | Skelnik et al. |
|---|---|---|---|---|
| 5,641,479 | A | * | 6/1997 | Linares et al. |
| 6,056,950 | A | | 5/2000 | Saettone et al. |
| 6,063,757 | A | * | 5/2000 | Urso |

FOREIGN PATENT DOCUMENTS

| DE | 38 27 477 A1 | | 2/1990 |
|---|---|---|---|
| EP | 0312208 A1 | * | 9/1988 |
| EP | 0 572 364 A2 | | 12/1993 |
| WO | WO 92/15614 | | 9/1992 |

OTHER PUBLICATIONS http://www.wrongdiagnosis.com/d/deafness/book-diseases-9a.htm. Torto, M. et al., Keratitis-Ichthyosis-Deafness Syndrome (NORD Guide to Rare Disorders). Downloaded Aug. 15, 2007.*
http://www.revoptom.com/archive/OP/op_040907.htm. Epstein, A. B. Optometric Physician™. Downloaded Aug. 15, 2007.*
http://www.nlm.nih.gov/medlineplus/ency/article/000426.htm. Medline Plus®. Medical Encyclopedia: Dry eye syndrome. Downloaded Aug. 15, 2007.*
Suresh, P. S. et al. Indian Journal of Ophthalmology (1999), 47(3): 155-165. Herpes simplex keratitis.*
Chemical Abstracts, Lambiase, Alessandro et al., "Increased Plasma Levels of Nerve Growth Factor in Vernal Keratoconjunctivitis and Relationship to Conjunctival Mast Cells", Sep. 1995, vol. 136, No. 10, pp. 2127-2132.
Chemical Abstracts, Lambiase, Alessandro et al., "Nerve Growth Factor Delays Retinal Degeneration in C3H Mice", Nov. 4, 1996, vol. 125, No. 19.

* cited by examiner

*Primary Examiner*—Michele C. Flood
(74) *Attorney, Agent, or Firm*—Young & Thompson

(57) ABSTRACT

The nerve growth factor (NGF) is used for the storage of corneas in culture, for the production and the storage in vitro of single cell populations of the corneal morphological and functional unit (i.e. epithelium, stroma/keratocytes and endothelium) and of the conjunctival epithelium, and for the production and the storage of corneal and conjunctival tissues, in particular for transplantation purposes. The NGF is also proposed for use in the therapy and/or the prophylaxis of diseases of the corneal surface, wherein a lack of integrity of the corneal and conjunctival morphological and functional unit occurs, in particular for pathologies having a dystrophic or neurodystrophic basis, both congenital and acquired.

17 Claims, No Drawings

USE OF NERVE GROWTH FACTOR FOR THE STORAGE, CULTURE OR TREATMENT OF CORNEA

The present invention relates to the use of nerve growth factor for the storage of corneas in culture, the in vitro production of corneal and conjunctival tissues and the treatment of corneal and conjunctival diseases. More particularly, the invention concerns the use of the neurotrophin named nerve growth factor (NGF)—known for its ability of influencing the development, the regeneration and the maintenance of the biological functions of neurons—for the treatment of corneal and conjunctival tissues, both for properly maintaining their functionality in vitro and for the therapy of pathologies of the ocular surface.

As it is known, corneal graft represents the only therapeutic approach to dystrophic, inflammatory or degenerative corneal diseases in the event that the said diseases have irreversibly compromised the transparency or the normal structure of the cornea. Once isolated from cadaver, the corneas are "stored" up to the time when they are transplanted, by means of storage methods employing liquids derived from cell culture mediums. According to one of the most common methods, called "short/intermediate term storage", the cornea is kept at 4° C. in culture mediums such as McCarey-Kaufman (MK) medium, or in different commercial liquids (among which Optisol-GS®), for a maximum period of 7 days. A longer term storage is possible with an equally common method, referred to as "organ culture". This method is based on techniques similar to cell culture, and allows to store the explanted corneas, at temperatures comprised between 30 and 36° C., for more than one month.

None of the above methods affords an improvement of the biological features of the corneal tissues with the storage, the best result achievable being that of maintaining unchanged the quality of said tissues during the storage. This cooperates in making even more critical the already difficult situation in the field of corneal graft. Actually, more than one half of the corneas are discarded upon explantation, since the microscope examination shows them to be unsuitable for transplant.

Another major problem is represented by the need of having available single corneal cell populations, such as endothelial cells, epithelial cells and keratocytes, so as to be able to use them for transplantation. In particular situations involving the destruction of the ocular surface due to physical or chemical burns, or resulting from synechiating autoimmune diseases (such as cicatricial pemphigoid, Stevens-Johnson syndrome, etc.) or from post-infectious pathologies, it is of a critical importance to have available corneal epithelial cells (including stem cells) to be transplanted in place of the damaged ocular surface, and/or to have available conjunctival epithelial tissue for use in replacing the synechiated and retracted surface.

Considering the pathological situations that may affect the morphological and functional unit consisting of cornea (i.e., epithelium, stroma/keratocytes and endothelium) and conjunctiva, it is noted that there is a wide variety of disorders affecting this region which are, to date, of a difficult therapeutic approach, or are totally orphan of a valid treatment. Such pathologies or situations which may interfere with the normal surface integrity include all the impairments of the tear film functions, congenital or acquired corneal and/or conjunctival affections such as: neurotrophic and neuroparalytic keratitis and/or conjunctivitis; post-traumatic, post-infectious, post-surgical keratitis and/or conjunctivitis; keratitis and/or conjunctivitis due to laser treatment, to chemical, physical or metal burns; autoimmune, dystrophic, degenerative, post-inflammatory keratitis. These diseases appear with alterations of the corneal epithelium (spontaneously in the primary neuroparalytic forms or on a physical, infectious, immune or toxic basis in the secondary forms) which may end in an ulcer, leading in most cases to corneal perforation, either spontaneously or following microtraumas or superinfections. The clinical picture of this disease is characterised by a slow and difficult recovery, by superinfections and by the frequent failure of any therapy. The final outcome is often the opacification of the cornea, or the spontaneous perforation thereof.

The above diseases are generally treated by having recourse to bandage and to the use of lubricating substances and antibiotics, with a view to prevent the complications. The conjunctival covering is necessary when the perforation is imminent or has already occurred, and has the only purpose of preserving the anatomic integrity of the eyeball, while the visual function is sacrificed. The corneal graft, both by lamellar and by penetrating keratoplasty, is absolutely contra-indicated in view of the frequent occurrence of relapses even on the transplanted graft, and in view of the risk of superinfections. On the basis of in vitro studies the topical medical treatment with preparations containing fibronectin, plasmin, collagenase inhibitors, EGF (i.e., epidermal growth factor), autoserum has also been proposed. None of these drugs turned out to be resolutive, or able to block or to reduce the corneal injury, or to modify the final outcome of the pathology.

In particular, in the treatment of corneal burns quite good results have been obtained with the transplantation of marginal conjunctiva taken from the contra-lateral eye. When the affection is bilateral, recourse may be had to the donation of conjunctiva by close relatives or, when this is not possible, to the excision from cadaver. However, this method is not resolutive in the totality of the cases. In the case of autograft relapses of the disease may occur after years, while in the case of homograft rejection is frequent, and an immunosuppressive therapy is absolutely necessary, with the well-known consequences due to the side-effects.

Another kind of corneal-conjunctival diseases the treatment of which often gives unsatisfactory results are the herpetic infections. After the resolution of a first pathologic occurrence, herpetic infections often give rise to relapses, the prevention and the treatment of which are often unsuccessful.

Also the diseases affecting the corneal endothelium, such as, e.g. primary and secondary decompensation and endothelitis, characterised by a loss in the number and/or in the function of endothelial cells, represent a group of affections which presently lack any effective treatment.

Therefore, it is a primary object of the present invention to provide a solution to the problems referred to above—which problems are all related to the physiopathology of the corneal and conjunctival morphological and functional unit—by means of the use of a therapeutic agent allowing to maintain and restore the proper biological activity of the said tissues.

The molecule known as nerve growth factor (NGF) is the first component of a complex family of neurotrophins, and is well-known for its trophic, tropic and differentiating action on cholinergic neurons of the central nervous system and on the peripheral sympathetic system. NGF is produced in several tissues in mammals, including man, and is released in the blood stream at higher levels during the growth and the differentiation of the nervous system. Biological, biochemical and molecular studies carried out in vitro on cell systems have evidenced a very high homology between murine NGF and human NGF. In man as in other animal species the NGF is normally present both in the cerebrospinal fluid and in the blood stream at levels of about 10-50 pg/ml. Said concentrations increase in some inflammatory pathologies (autoimmune diseases, allergic diseases, etc.) and decrease in other pathologies (diabetes).

The NGF was discovered in 1951 by Prof. Rita Levi-Montalcini, of the Zoology Institute of the Washington University of St. Louis (see Levi-Montalcini R., Harvey Lect., 60:217, 1966) and represented a major advance in the study of the growth and differentiation mechanisms of the nerve cell, as it is capable of influencing the development and the maintenance of the biological functions of neurons and their regeneration. For the discovery of this molecule, for having characterised its biological role both in the peripheral nervous system and in the central nervous system, Prof. R. Levi-Montalcini was awarded in 1986 the Nobel prize for Medicine and Physiology.

Several experimental studies, both in vitro and in vivo, have shown the physiopathological importance of the NGF in preventing neuronal injury of a surgical, chemical, mechanical and ischemic nature, thereby making it the ideal candidate for use in the therapy of several diseases of the central and peripheral nervous system (Hefti F., J. Neurobiol., 25:1418, 1994; J. Fricker, Lancet, 349:480, 1997). Indeed, clinical trials on patients suffering from Parkinson's disease and from Alzheimer's disease have already started since some years. Said trials are carried out by intracerebral administration of murine NGF (see, e.g., Olson L. et al., J. Neural Trans.: Parkinson's Disease and Dementia Section, 4: 79, 1992). The results of the said studies confirmed the observations made on animal models and evidenced the absence of any possible side-effects upon administration of murine NGF. This feature has more recently been confirmed as regards human recombinant NGF (Petty B. G. et al., Annals of Neurology, 36:244-246, 1994).

Ever since its discovery, the studies on the NGF, i.e. on the characterisation of its biological, biochemical, molecular, preclinical and clinical effects have been carried out almost exclusively with NGF isolated from the submaxillary glands of adult rodents; thus, the widest amount of data acquired to date concerns murine NGF. The biochemical properties of the latter have been described, in particular, in a work dating back to 1968 (Levi-Montalcini R. and Angeletti P. U., Physiological Reviews, 48:534, 1968).

The NGF contained in the salivary glands of mice is a 140 kdalton molecular complex, with sedimentation coefficient 7S, consisting of three subunits, $\alpha$, $\beta$ e $\gamma$, the second one of which represents the true active form. This sub-unit, called $\beta$NGF, with sedimentation coefficient 2.5S, is normally extracted and purified according to three methods which are not very different from each other (Bocchini V., Angeletti P. U., Biochemistry, 64: 787-793, 1969; Varon S. et al., Methods in Neurochemistry, 203-229, 1972; Mobley W. C. et al., Molecular Brain Research, 387: 53-62, 1986).

The $\beta$NGF obtained with such methods is in turn a dimer of about 13,000 dalton, consisting of two identical chains of 118 amino acids. Each single chain is stabilised by three disulphide bridges, while non-covalent bonds provide to the formation of the dimer structure. This molecule, being very stable, may dissolve in almost every solvent, both aqueous and oily, while keeping unaltered its biochemical features and its biological activity. Further information on the structure and the physical and biological properties of the molecule can be found in Greene, L. A. and Shooter, E. M., Ann. Rev. Neurosci. 3:353, 1980.

Recently, the structure of the $\beta$NGF has been further elucidated by means of a crystallographic analysis. The latter detected the presence of three antiparallel couples of strands, with secondary structure of the $\beta$ kind, which co-operate in forming a planar surface along which the two chains associate to form the active dimer. On said chains of the $\beta$NGF there has been evidenced the presence of four loop regions containing many variable amino acids. To these variable amino acids is connected, very likely, the specificity of the recognition by the receptor.

The biological effect of the NGF is mediated by two receptors present on the surface of the respective target cells. There are several antibodies which selectively inhibit the biological action of NGF. The existence of the said antibodies has allowed and allows to accurately characterise and modulate the NGF activity, both in cell systems and in vivo.

In more recent times it has become possible to synthesize human NGF with genetic engineering techniques (Iwane, M. et al., Biochem. Biophys. Res. Commun., 171:116, 1990), and small amounts of human NGF have been placed on the market. However, direct experimentation has shown that the biological activity of human NGF is quite low in comparison with the biological activity of murine NGF. In addition, it is to be considered that almost all of the data presently available on the effects on man, both in vitro and in vivo, have been obtained by using murine NGF, and that no adverse effects have been detected which may be connected to the murine origin of the product.

Studies carried out starting from the nineties on animal models suggested a possible involvement of the NGF in ocular pathologies. However, such studies almost exclusively concern the use of NGF in retinal affections, i.e. on the nervous tissue, while nothing is present in the literature about an effect of this neurotrophin on the ocular surface (i.e., cornea and conjunctiva), nor are there any scientific works proposing the use of the NGF for the treatment of diseases affecting the cornea and/or the conjunctiva. In particular, some studies have been carried out on animals in order to ascertain the effect of the topical administration of NGF in the treatment of retinal pathologies, for instance in the treatment of acute retinal ischemy (Siliprandi R. et al., Inv. Ophthalmol. Vis. Sci., 34:3232, 1993), in the transection of the optical nerve (Carmignoto G. et al., J. Neurosci., 9:1263, 1989) and in the treatment of retinitis pigmentosa (Lambiase A. e Aloe L., Grafe's Arch. Clin. Exp. Ophthalmol., 234: S96-S100, 1996). The results demonstrated that the topical administration of NGF can prevent, or at least delay, the death of the retinal ganglion cells and of the photoreceptors during the above pathologies. None of these studies evidenced side-effects on animals.

On the other hand, with reference to the diseases of the corneal tissues which are the object of interest of the present invention, several Authors have considered for such indications the possible employment of the epidermal growth factor (EGF), starting from the assumption that alterations of the corneal epithelium represent the pathogenic key to the development of other corneal affections, such as ulcers and keratites.

The EGF is a 53 amino acid polypeptide discovered and characterised in the early sixties (Cohen S., J. Biol. Chem., 237:1555-1562; 1962), having a molecular weight of about 6000 dalton. Said molecule is produced by the salivary gland of adult mice, but is present in small amounts in many human tissues. The EGF exerts a well-characterised trophic, prolipherative and differentiative action on the epithelial cells obtained from various animal and human tissues, and its in vitro effectiveness on corneal epithelial cell cultures, as well as its capacity of inducing proliferation and differentiation of these cells are described in some experimental works.

However, the clinical studies on corneal diseases which have been carried out on the basis of the above experimental data gave contradictory results, and showed, in general, a substantial ineffectiveness of the EGF in this kind of human diseases (Kandrakis A. S. et al., Am. J. Ophthalmol., 98:411, 1984). The said ineffectiveness may be ascribed, probably, to a different expression of the EGF receptor in vitro and in vivo or, more likely, to the fact that epithelial alterations in corneal diseases would only represent an epiphenomenon of the corneal disease itself.

EP-A-0 312 208 (Ethicon) discloses gel formulations for use in the treatment of epithelial lesions and epithelial pathologies in general, including lesions and pathologies of the ocular surface. The said formulations contain an active ingredient which may be indiscriminately chosen among the various molecules whose name contains the expression "growth factor". Although the description is exclusively concerned with the EGF as the preferred active ingredient, and although activity data (in vitro) and formulation examples are given only for the EGF, other growth factors are mentioned as well, such as FGF (fibroblast growth factor), PDGF (platelet-derived growth factor), TGF-α (transforming growth factor) or the NGF itself. The said growth factors are apparently presented as a family of molecules having the same features and the same biological activity as the EGF. As a matter of fact, at the current state of the knowledge, the expert is aware that the said growth factors have different specific targets and that they often have conflicting effects, and does not consider the said growth factors as biologically equivalent to each other. Besides, as far as the ophthalmic field is specifically concerned, the above document describes the said growth factors as active exclusively on the corneal epithelium, thus reducing the proposed indication to an indication as re-epithelizing factors, useful, in practice, only in traumatic affections.

On the contrary, the studies that lead to the present invention started from the concept of cornea as a morphological and functional unit, wherein the single layers (i.e. epithelium, stroma and endothelium) all carry out a function of an equal importance in the preservation of the tissues integrity and in the recovery mechanisms. In this perspective, a key role is played by the trophic support offered by the corneal sensory innervation, whose damage brings about a damage to the whole morphological and functional unit.

In view of the fact that no evidence existed in the prior art of an effect of the NGF (i.e., one of the many mediators released by the sensory endings in other regions of the body) on the ocular surface, the question has been initially posed whether such neurotrophin might play a trophic-reparatory action on the corneal tissue of neuroectodermal embryonal derivation, since several targets of the said neurotrophin show a similar embryogenetic derivation. Thus, cornea and conjunctiva have been analysed for the presence of the NGF and of the NGF high affinity receptor (TrkA, tyrosine kinase A), using a monoclonal antibody (TrkA-antibody; Santa Cruz, USA) with immunohistochemistry techniques (Bhattacharyya A. et al., J. Neurosci. 17:7007, 1997). In fact, the presence of the specific receptor is a key requirement for the activity of the molecule under examination.

It has thus been found that all of the corneal cells (i.e., epithelial cells, endothelial cells and keratocytes) express TrkA and that, at the same time, the corneal somatosensory innervation is able to release NGF. This discovery allows to hypothesise, on one hand, that the NGF, probably released by the nerve endings, would play a physiopathologic role in all corneal reparative mechanisms (both at the surface and at a deeper level) and, on the other hand, that several superficial corneal diseases accompanied by primary damage to the innervation (such as neurotrophic or dystrophic keratitis and recurrences of herpetic infections) or with secondary damage to the innervation (such as chemical or physical burns and post-infectious, autoimmune, post-surgical lesions, or lesions resulting from laser treatment) would admit as a fundamental etiologic step the lack of NGF release.

The same finding also allows to hypothesise that the NGF would be essential to the maintenance of the whole corneal tissue in culture, i.e. in all such conditions wherein the cornea as a whole, intended as a morphological and functional unit comprising epithelium, stroma and endothelium, or some cells thereof, are deprived of the trophic support provided by the release of the NGF by the corneal nerve endings.

In addition, since the effects that have been observed after administration of exogenous NGF occur at concentrations close to the physiological level it can be hypothesised that a possible physiopathogenic mechanism in the corneal affections considered herein consists in a reduction of the local levels of the NGF below the threshold capable of assuring the corneal and/or conjunctival integrity.

Accordingly, the present invention specifically provides, according to a first aspect thereof, the use of the nerve growth factor for the storage of corneas in culture and for the storage and the production in vitro of corneal and conjunctival tissues, and of single corneal or conjunctival cell populations.

Preferably, the NGF is added to a culture medium of the kind suitable for the storage of corneas, or for the in vitro culture of corneal or conjunctival cells or tissues, in amounts comprised between 100 pg/ml and 200 ng/ml, optionally together with other nutrients and other biologically active agents. The NGF to be used to that aim can be of a murine or human origin, including recombinant NGF, and it may be used in lyophilised form, dissolved in solution, in a culture medium or in any other available solvent, so as to obtain a final concentration comprised in the range specified above.

Suitable methods of extracting and purifying the NGF are reported in the literature mentioned above. For the purpose of experimenting the present invention, the Bocchini and Angeletti technique (cited above) has been adopted, the latter being synthetically set forth below. The submaxillary glands of adult male mice are explanted under sterile conditions and the tissues are homogenised, centrifuged and dialysed; then the suspension is passed through subsequent cellulose columns, thereby separating the NGF by adsorption. The NGF is then eluted from the column by means of a buffer containing 0.4 M sodium chloride. The samples so obtained are analysed by spectrophotometer at a wavelength of 280 nm to identify the NGF-containing fractions. The latter are dialysed, and the NGF thus obtained is lyophilised under sterile conditions and kept in refrigerator at −20° C.

In an evaluation of the effects of an addition of NGF to various culture mediums for explanted corneas (both at 4° C. and at 30-36° C.), a general improvement of the biological features of the corneal tissue has been obtained with amounts of NGF comprised between 100 pg/ml and 200 ng/ml. The optimal response has been obtained with a concentration of about 100 ng/ml. Specifically, after 7 days of culture the improvements obtained were an increase of the endothelial cells density (increase from 10 to 25%), a reduction of the endothelial cells mortality (absence of trypan blue positive endothelial cells), a better endothelial morphology (i.e., quantitatively, a 3/3 trophism vs. a 2/3 trophism in the controls without addition of NGF), a higher viability of the keratocytes and a remarkably better appearance of the epithelium. In addition, some corneas that before being placed in culture were considered not suitable for transplantation turned out to be suitable after being cultured for 7 days in presence of NGF.

A similar experimental evaluation of the effects of the NGF as additive in the culture medium of corneal cells (i.e., epithelial cells, endothelial cells and keratocytes) showed that the addition of murine NGF in amounts comprised between 100 pg/ml and 200 ng/ml (with an optimal response at the concentration of about 100 ng/ml) induces the proliferation and differentiation of the various cell populations, and, moreover, it assists the rooting of the said cell populations on a number of supporting tissues (such as lamellae of corneal stroma, amniotic membrane, etc.). Further, such addition favours the interaction between the different cell types in cell co-cultures. Thus, the invention may be also employed for culturing mixed corneal cell lines in order to obtain an artificial cornea useful for transplantation.

Also the conjunctival epithelial cell cultures have shown a proliferation and differentiation increase, as well as an increase in the number of goblet cells, when cultured in presence of murine NGF at the same concentrations specified above. The graft of epithelial conjunctival tissue thus obtained is extremely advantageous for replacing the conjunctiva of patients suffering from kerato-conjunctivitis sicca (dry eye syndrome), both primary and secondary to other pathologies.

According to another aspect of the invention, there is provided, therefore, a culture medium for the storage of corneas or for the storage and the production in vitro of corneal and/or conjunctival tissues, or of single corneal or conjunctival cell populations, characterised in that it contains an effective amount of NGF, preferably comprised between 100 pg/ml and 200 ng/ml, most preferably about 100 ng/ml.

As set forth before, according to a further aspect of the invention there is provided the use of the nerve growth factor in the manufacture of a medicament for the therapy and/or the prophylaxis of corneal and/or conjunctival diseases.

Specifically, the invention is useful for the production of medicinal products suitable for the treatment and/or the prophylaxis of congenital and/or acquired corneal and/or conjunctival diseases chosen from the group consisting of: neurotrophic and neuroparalytic keratitis and/or conjunctivitis; herpetic keratitis and/or conjunctivitis; post-traumatic, post-infectious, post-surgical keratitis and/or conjunctivitis; keratitis and/or conjunctivitis due to impairment of the tear film functions, to laser treatment, to chemical, physical or metal burns; autoimmune, dystrophic, degenerative and post-inflammatory keratitis.

Preferably, a medicinal product according to the invention suitable for topical administration contains, alone or in combination with one or more other active ingredients, from 10 to 500 μg of NGF per ml, an optimal concentration being about 250 μg of NGF per ml. Such product may be in the form of opthalmic solution for eye-drops, or in the form of a gel, an ointment, a cream or a powder, or it can be added to a local bandage or to a medicinal contact lens.

According to another embodiment of the invention, the pharmaceutical product for the manufacture of which the NGF is proposed is a medicament indicated for the therapy and/or the prophylaxis of primary and secondary endothelial ophthalmic pathologies. For this use, the preferred formulations contain (also in this case optionally in combination with other active ingredients) from 1 to 250 μg of NGF per ml, and the administration is carried out by introduction in the anterior chamber of the eye.

In vivo studies on animals concerning the treatment of disorders of the corneal endothelium have been carried out by administration in the anterior chamber of the eye of aqueous solutions containing NGF at concentrations comprised between 1 and 250 μg/ml. In particular, in rabbits wherein an endothelial damage had been introduced by means of a cryoprobe a complete restoration of the endothelial density has been obtained after 15 days of treatment with NGF. The administration of NGF in endothelial pathologies, both of a dystrophic nature and acquired, both with loss of the number of endothelial cells and with loss of the functionality thereof, has been shown to restore a proper endothelial function.

In a series of studies on man for ascertaining the efficiency of the treatment with NGF in the topical treatment of cornea and/or conjunctival affections, a number of pathologies have been selected on the basis of a primary or secondary involvement of the somato-sensorial corneal nerve plexus. Murine NGF (2.5S), obtained with the purification method summarised above, has been employed in such studies. The NGF has been topically administered at a concentration of about 250 mg/ml, diluted in balanced salt solution.

The table shown further on summarises the results obtained from a study on 5 patients affected by torpid corneal ulcer due to neurodistrophic keratitis (2 eyes), or after keratoplasty (2 eyes) or due to burn by alkali (2 eyes). The therapeutic schedule consisted in the instillation of one-two drops of the preparation of the invention with a daily frequency divided as follows: every 2 hours for the first 2 days, 6 times a day up to the 2nd day after the complete re-epithelization of the cornea and twice a day for the following 15 days.

The topical treatment with the NGF was started after 15 days of treatment with autoserum, in the absence of signs of improvement of the clinical picture. All of the patients treated showed clear signs of recovery within 2 weeks from the start of the treatment with NGF, and none of them evidenced any occurrence of local or systemic side-effects during the treatment or in the following period. Once suspended, the therapy should be immediately restored in the event that the first signs or symptoms of any relapse of the epithelial pathology appear.

The concerned 5 cases are discussed in detail below, and the main data are summarised in the following table.

1 st Case—A 9-year-old female, affected by a congenital anophtalmos, showed in the other eye a corneal ulcer since more than 20 days. The said ulcer, topically treated with antibiotics and steroids, did not show any tendency to healing. The ulcer was about 7 mm in diameter and more than ⅔ of the corneal stroma in depth. The clinical examination showed corneal anaesthesia, on the basis of which a neurotrophic keratitis was diagnosed. After 15 days of treatment with autoserum, having ascertained a progressive worsening of the clinical picture, the topical treatment with NGF was started.

After 4 days the corneal ulcer was reduced to about a 3.5 mm in diameter, and after 12 days the cornea was completely healed and the treatment with the NGF was discontinued. The patient showed a central leukoma with some neo-vessels and, although reduced, a corneal sensitivity was present, while it was completely absent before the treatment. After a 8 months follow-up the patient showed 5/10 of visual acuity and the corneal sensitivity was still present.

2nd Case—A 26-years-old woman, affected by syndactilia and deficit of the VIII pair of cranial nerves, showed since about 2 months a corneal ulcer which progressively deepened until it reached an extent of 7 mm and a depth up to the Descemet membrane. The clinical examination showed a complete corneal anaesthesia.

After 2 weeks of therapy with the NGF apparent signs of recovery were present, with a reduction in the ulcer depth. After 6 weeks of therapy the cornea was completely re-epithelized, while a central leukoma with some neo-vessels was left. In addition, some corneal sensitivity was recovered, although reduced.

remained re-epithelized, and the visual acuity of the right eye was 3/10, while that of the left eye was 1/10. In addition, a corneal sensitivity was still present in both eyes.

TABLE 1

Treatment in vivo with Nerve Growth Factor

| Patient No. | Pathology | Age (years), sex | Time from onset | Initial sensitivity | Previous therapy | Treatment with NGF | Outcome | Final sensitivity | Visus | Follow up |
|---|---|---|---|---|---|---|---|---|---|---|
| 1 | neurotrophic ulcer | 9, F | 20 days | anaesthesia | antibiotics, steroids, auto-serum | 12 days | recovery | normal/hypoesthesia | improved | 8 months |
| 2 | neutrophic ulcer | 26, F | 2 months | anaesthsia | antibiotics, steroids, auto-serum | 6 weeks | recovery | normal/hypoesthesia | improved | 4 months |
| 3 | neurotrophic ulcer in PK[a)] | 25, M | 1 month | anaesthesia | antibiotics, auto-serum | 4 weeks | recovery | anaesthesia | improved | 2 months |
| 4 | post (burn by alkali) ulcer in LK[b)] | 56, M | 2 months | anaesthesia | antibiotics, auto-serum | 5 weeks | recovery | normal/hypoesthesia | improved | 4 months |
| 5 (RE) | post (burn by acid) ulcer | 56, M | 1 month | anaesthesia/hypoesthesia | antibiotics, auto-serum | 2 weeks | recovery | normal/hypoesthesia | improved | 3 months |
| 5 (LE) | post (burn by acid) ulcer | 56, M | 1 month | anaesthesia/hypoesthesia | antibiotics, auto-serum | 3 weeks | recovery | normal/hypoesthesia | improved | 3 months |

[a)]PK: corneal graft by penetrating keratoplasty
[b)]LK: corneal graft by lamellar keratoplasty 3rd Case—A man aged 25, who had undergone enucleation of the left eye following the onset of a corneal ulcer after a penetrating keratoplasty, showed since about 1 month a corneal ulcer in the right eye, into a corneal graft. The corneal ulcer was about 5 mm in diameter and its depth was ½ of the corneal stroma. Corneal anaesthesia was also present.

After 2 weeks of treatment with NGF a corneal healing process was evident, with reduction of the extent and the depth of the ulcer. After 4 weeks of treatment with NGF the ulcer was completely healed and a central leukoma with some neo-vessels was left. A marked corneal hypoesthesia was still present.

4th Case—A 56-years-old man showed a bilateral corneal ulcer due to a burn by alkali. The right eye, after having undergone surgery by penetrating keratoplasty, had been enucleated after the onset of an ulcer. The left eye, after-undergoing lamellar keratoplasty, developed a torpid ulcer of about 7 mm in diameter, which did not show any sign of healing.

After 2 weeks of treatment with NGF the onset of a recovery process was evident, and the said process was complete after 5 weeks.

5th Case—A 56-years-old man showed a bilateral corneal ulcer due to a burn by hydrochloric acid. In the right eye an ulcer of about 4 mm in diameter was present, while in the left eye the ulcer was bigger (more than 8 mm in diameter) and deeper. The patient showed a marked corneal hypohestesia.

After 2 weeks of treatment with NGF the right eye was completely healed, with a residual central leukoma, while the ulcer in the left eye was reduced both in extent and in depth, although a neo-vessel pannus was present. After 3 weeks of treatment both corneas were fully re-epithelized, a central leukoma was left and corneal sensitivity was present, although reduced. After a 2 months follow-up both corneas The foregoing data clearly show the effectiveness of the use of the NGF not only for storing and producing in vitro corneal and/or conjunctival tissue, as a whole or partially, or for storing and producing in vitro the single cell types of which the said tissues consist, but also for treating and preventing human or animal diseases affecting the corneal morphological and functional unit or the conjunctiva, which diseases have not found, so far, an effective therapy.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method for the treatment of autoimmune keratitis, dystrophic keratitis, or degenerative keratitis in a subject, comprising:
    topically administering an effective amount of nerve growth factor to an eye of said subject to treat said autoimmune keratitis, dystrophic keratitis, or degenerative keratitis, and wherein the nerve growth factor is administered as a medicament comprising 10 to 500 µg nerve growth factor per milliliter.

2. The method according to claim 1, wherein the medicament comprises nerve growth factor in an amount of about 250 µg nerve growth factor per milliliter.

3. The method according to claim 1, wherein the medicament comprises one or more active ingredients in addition to the nerve growth factor.

4. The method according to claim 1, wherein the nerve growth factor is of murine origin.

5. The method according to claim 1, wherein the nerve growth factor is of human origin.

6. The method according to claim 1, wherein the nerve growth factor is human recombinant nerve growth factor.

7. A method for treating autoimmune keratitis, dystrophic keratitis, or degenerative keratitis in an eye of a subject, comprising administering to said eye of said subject a composition comprising 10 to 250 µg of nerve growth factor per milliliter.

8. The method according to claim 7, wherein said subject is administered a composition comprising about 250 µg nerve growth factor per millimeter.

9. The method according to claim 7, wherein said subject is treated for autoimmune keratitis.

10. The method according to claim 7, wherein said subject is treated for dystrophic keratitis.

11. The method according to claim 7, wherein said subject is treated for degenerative keratitis.

12. The method according to claim 9, wherein the composition is administered in drops with a daily frequency of every two hours for the first two days, six times a day up to the second day after complete re-epithelization of the cornea and twice a day for the following 15 days.

13. The method according to claim 10, wherein said composition is administered in drops with a daily frequency of every two hours for the first two days, six times a day up to the second day after complete re-epithelization of the cornea and twice a day for the following 15 days.

14. The method according to claim 11, wherein the composition is administered in drops with a daily frequency of every two hours for the first two days, six times a day up to the second day after complete re-epithelization of the cornea and twice a day for the following 15 days.

15. The method according to claim 7, wherein the nerve growth factor is of murine origin.

16. The method according to claim 7, wherein the nerve growth factor is of human origin.

17. The method according to claim 7, wherein the nerve growth factor is human recombinant nerve growth factor.

* * * * *